(12) United States Patent
Hang (10) Patent No.: US 9,744,005 B2
(45) Date of Patent: Aug. 29, 2017

(54) ANTERIOR DEVELOPMENT AND POSTURAL TRAINER

(71) Applicant: William M. Hang, Westlake Village, CA (US)

(72) Inventor: William M. Hang, Westlake Village, CA (US)

( * ) Notice: Subject to any disclaimer, the term of this patent is extended or adjusted under 35 U.S.C. 154(b) by 384 days.

(21) Appl. No.: 14/339,806

(22) Filed: Jul. 24, 2014

(65) Prior Publication Data

US 2014/0335465 A1 Nov. 13, 2014

Related U.S. Application Data (63) Continuation-in-part of application No. 12/731,649, filed on Mar. 25, 2010, now Pat. No. 9,011,145.

(51) Int. Cl.
| | |
|---|---|
| *A61C 3/00* | (2006.01) |
| *A61C 7/36* | (2006.01) |
| *A61C 7/10* | (2006.01) |
| *A61C 7/00* | (2006.01) |

(52) U.S. Cl.
CPC .................. *A61C 7/36* (2013.01); *A61C 7/00* (2013.01); *A61C 7/10* (2013.01)

(58) Field of Classification Search
CPC .... A61C 7/08; A61C 7/00; A61C 7/10; A61C 7/36
USPC ....................................................... 433/6, 7
See application file for complete search history.

(56) References Cited

U.S. PATENT DOCUMENTS

| | | | |
|---|---|---|---|
| 3,871,370 A | 3/1975 | McDonald | |
| 4,026,023 A * | 5/1977 | Fisher ...................... | A61C 7/10 433/7 |
| 4,669,459 A * | 6/1987 | Spiewak ................. | A61F 5/566 128/848 |
| 4,901,737 A * | 2/1990 | Toone ..................... | A61F 5/566 128/848 |
| 5,002,485 A * | 3/1991 | Aagesen .................. | A61C 7/10 433/18 |
| 5,096,416 A * | 3/1992 | Hulsink ................... | A61C 7/08 433/6 |
| 5,884,625 A | 3/1999 | Hart | |
| 5,915,385 A | 6/1999 | Hakimi | |
| 5,950,624 A | 9/1999 | Hart | |
| 6,435,871 B1 * | 8/2002 | Inman ...................... | A61C 7/00 433/21 |
| 6,467,484 B1 | 10/2002 | De Voss | |
| 6,505,625 B1 * | 1/2003 | Uenishi .................... | A61C 7/08 128/848 |
| 6,766,802 B1 | 7/2004 | Keropian | |
| 7,001,180 B2 * | 2/2006 | Bass ........................ | A61C 7/10 433/18 |

(Continued)

*Primary Examiner* — Matthew Nelson
(74) *Attorney, Agent, or Firm* — Sanford Astor (57) ABSTRACT

An orthodontic appliance that postures the lower jaw forward and connects the lower jaw to the upper jaw, comprising two upper palate bases, a labial bow located in a front region of the appliance, a lower incisor support wire located in a front region of the appliance, an upper incisor support wire located in the a front region of the appliance, a lateral incisor support wire, cuspid support wires located in a front region of the appliance, a palatal bar which connects the two bases of the appliance, and landing gear reminders to engage the soft tissue covering the mandible.

18 Claims, 8 Drawing Sheets

(56) References Cited

U.S. PATENT DOCUMENTS

| | | | |
|---|---|---|---|
| 7,661,955 B2* | 2/2010 | Da Cruz | A61C 7/10 433/18 |
| 8,122,889 B2 | 2/2012 | Vaska et al. | |
| 8,127,769 B2 | 3/2012 | Walker | |
| 8,132,567 B2 | 3/2012 | Keropian | |
| 2003/0124479 A1* | 7/2003 | Bass | A61C 7/10 433/19 |
| 2007/0059659 A1* | 3/2007 | Da Cruz | A61C 7/10 433/6 |
| 2007/0224567 A1* | 9/2007 | Robson | A61F 5/566 433/6 |
| 2007/0240724 A1* | 10/2007 | Bergersen | A61C 7/08 128/861 |
| 2008/0057457 A1* | 3/2008 | Inman | A61C 7/20 433/6 |
| 2008/0220388 A1* | 9/2008 | Weissbach Otte | A61C 7/10 433/7 |
| 2010/0163043 A1 | 7/2010 | Hart et al. | |
| 2011/0236847 A1* | 9/2011 | Hang | A61C 7/10 433/6 |
| 2011/0269095 A1* | 11/2011 | Singh | A61F 5/566 433/24 |

* cited by examiner

ANTERIOR DEVELOPMENT AND POSTURAL TRAINER

This application is a continuation-in-part of U.S. application Ser. No. 12/731,649 filed Mar. 25, 2010, the disclosure of which is hereby incorporated in its entirety by reference herein.

TECHNICAL FIELD

This invention relates to a new and useful orthodontic appliance that postures the lower jaw forward, and connects the lower jaw to the upper jaw.

BACKGROUND

The "Anterior Development And Postural Trainer-Landing Gear Reminder" referred to herein as (ADAPT-LGR) is a new appliance used as part of an overall treatment called Orthotropics®, which was developed about 50 years ago. It is a treatment which recognizes that all malocclusions have the common feature of the upper jaw being recessed relative to an ideal. It recognizes that the major cause of malocclusion is poor rest oral posture, usually secondary to airway issues. Proper rest oral posture means that at rest 1) The teeth are lightly together 2) The tongue is firmly against the palate with the tip of the tongue immediately behind the upper front teeth 3) The lips are together without strain.

The first thing to happen in all malocclusions is that the upper front teeth are not properly supported by the tongue and these front teeth begin to fall down and back from their ideal positions in the face. The lower jaw will also fall down and back as the upper jaw falls back. The exact nature of every malocclusion depends on exactly how the jaws are held at rest. For instance, a patient who has their mouth hanging open all the time will likely develop a long face and an open-bite tendency. A patient who has the lips together, but the tongue postured between the back teeth will develop a deeper bite (front teeth overlapping) and probably a shorter face than someone whose lips are apart all the time. There are many types of malocclusions with different variations, but none would develop if the teeth at rest were together, the tongue to the palate, and the lips together without strain.

Many appliances in orthodontics have been used to try to develop the lower jaw forward. Many of them have originated in Europe and made their way to the U.S. at varying times over the past century. They are all called "functional appliances" in that their supporters feel that they are a changing "function" (active process). All of these appliances posture the lower jaw forward, and in one way or another, connect the lower jaw to the upper jaw. The process is generally referred to as Functional Jaw Orthopedics (FR)). All tend to have a "headgear effect". This means that the upper jaw will move back slowly over time as the muscles of the lower jaw pull the lower jaw back, the force from the lower jaw being applied through the appliance to the upper jaw. None of the proponents of these appliances suggest moving the upper jaw forward before attempting to move the lower jaw forward. The best case scenario is that they are attempting to move the deficient lower jaw forward to an already deficient upper jaw. With the headgear effect making the upper jaw even more deficient there is very little forward development of the lower jaw. Among the appliances which attempt to do this are the Bionator, Activator, Orthopedic Corrector, Herbst, Twin-Block, Forsus, MARA, Frankel, etc. There are other less common ones, as well.

Orthotropics® has a goal, not of changing "function" (an active process) but "posture" (an habitual rest position). The goal is to correct poor rest oral posture, and the approach is therefore called "postural". The appliances are "postural" appliances as opposed to "functional" appliances. The idea is that the jaw will ultimately assume the position it is held in most of the time. Orthotropics® has at its core the idea that the maxilla always needs to be developed upward and forward before the mandible is developed forward. This often involves moving the upper teeth forward 8-10 mm. prior to moving the lower jaw forward. In all cases the upper jaw is also expanded laterally dramatically (often in excess of 10 mm.) so that the tongue can ultimately be properly fit to the roof of the mouth and stay there. In many children today, the upper jaw has become so narrow due to poor rest oral posture that the tongue simply cannot fit into the palate and remain there at rest. The maxilla must be expanded so that the tongue can be placed there and learn to stay there at rest.

The Hang Expancer, described in the parent application, develops the maxilla laterally and anteriorly. After the maxilla has been properly developed upward and forward the patient has traditionally been given a Stage III or Stage IV Biobloc, (names for the appliances used for this purpose) to posture the lower jaw forward. They are similar to all "functional" appliances with one dramatic difference. The Stage III or Stage IV appliance has large plastic flanges which protrude down from the appliance to the floor of the mouth. They are called "soft locks" because they extend down to the soft tissue in the floor of the mouth. The flanges (or soft locks) are adjusted by adding acrylic or a hydroplastic material to the acrylic so that they "engage" the soft tissue of the lower jaw. If the jaw falls back these "soft locks" cause discomfort to the soft tissue and the patient must learn to keep their lower jaw ahead of them. The patient learns to posture their jaw in one single position that is dictated by the appliance because it is uncomfortable if they do not. If the patient does this long enough the lower jaw eventually ends up in that position.

Because a child will feel discomfort if their lower jaw falls back this negates or dramatically reduces the headgear effect of "functional" appliances. Because the maxilla has already been developed forward (with the Hang Expancer) and the headgear effect is eliminated or reduced with this appliance sequence, the face ends up with both jaws further forward. The jaws are more balanced and the airways have been shown to be better on average.

There are some very distinct disadvantages to the Stage III and Stage IV appliances, discussed above. Disadvantage number one is that they are big. The extensions which hang down ("soft locks") make the Biobloc appliances very large, and they look foreboding. Patients often say, "You're going to put that in my mouth". The best part of the new ADAPT-LGR appliance of this invention is that the appliance looks like a very slightly "fat" version of the retainer, which the patient is wearing after they have stopped wearing the Hang Expancer. A child is easily used to this appliance without any of the fear of, "that is too big for my mouth".

Disadvantage number two of the Stage III and Stage IV appliances, are that they cause gagging rather frequently. The posterior soft locks rather frequently cause the patient to gag when the appliance is first inserted. Sometimes this experience alone is enough to cause a child to terminate the treatment immediately.

Disadvantage number three is that the locks are there even though the patient doesn't need them initially. The soft locks are not needed when the appliance is first inserted. The soft locks are "activated" when the child is accustomed to wearing the appliance, usually about after a week or two.

Disadvantage number four is that the soft locks are not easy to move forward on the appliance and that must be often done. Many patients will have a space of 10+ mm. for the lower jaw to move forward. Orthodontists can only posture the lower jaw forward easily about 5-6 mm, at a time. The patient must learn to adapt to the moderately advanced position before they can tolerate the lower jaw even further forward. The "soft locks" on Stage III and Stage IV appliances are made in the position that is determined by the first positioning forward of the lower jaw. In subsequent adjustments of the lower jaw forward, the mandible can be postured further forward, but the "soft locks" on the appliance remain in that initial position. To really engage the lower jaw and cause the patient not to fall back, they must be adjusted forward and they are not easily adjustable. Adjustment can require a separate laboratory procedure where the appliance must be taken away from the patient for a few days to be reprocessed by the lab. This is expensive, time consuming and a waste of time. The doctor is inclined not to do it but will get less than superior results if they don't.

SUMMARY

The prior art problems discussed above are solved by the new features described below. Instead of the large "soft locks" used by the prior art, there are substituted the "landing gear reminders" which are folded up in "flying" position until they are needed. This is a major advantage over the prior art appliances.

The "landing gear reminders" can easily be bent forward and adjusted to the proper length with one twist of the pliers. The thermoplastic material can be adjusted again to fully engage the "landing gear reminders". The posterior 'reminders' overlap the anterior 'reminders' when they are folded in the "up" position.

The ADAPT-LGR, Landing Gear Reminders, are bent down to the proper position and then thermoplastic material is added which engages the soft tissue of the floor of the mouth. The patient's jaw is adjusted to the soft thermoplastic material when it is warm. It adapts intimately to the soft tissue of the floor of the mouth adjacent to the lower bicuspid teeth (anterior landing gear) and in the retromolar area (posterior landing gear.) Properly adjusted it can be made so that the patient must keep their jaw forward and cannot allow it to exert a pull back on the appliance and hence on the upper teeth and jaw.

BRIEF DESCRIPTION OF THE DRAWINGS

The foregoing and other objects, features and advantages of the invention will be apparent from the following more particular description of the embodiments of the invention, as illustrated in the accompanying drawing figures.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 2:
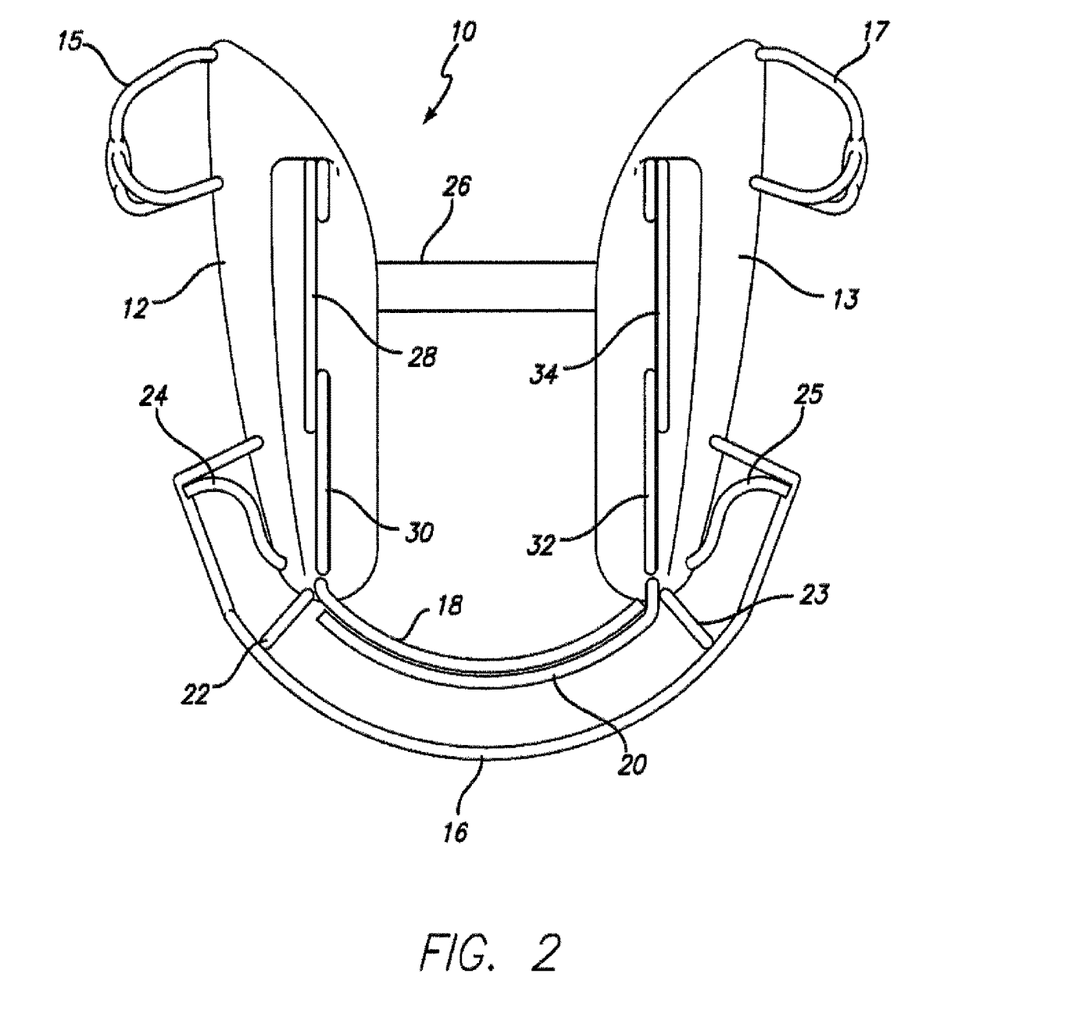
FIG. 2 is a bottom view of the appliance.
Figure 3:
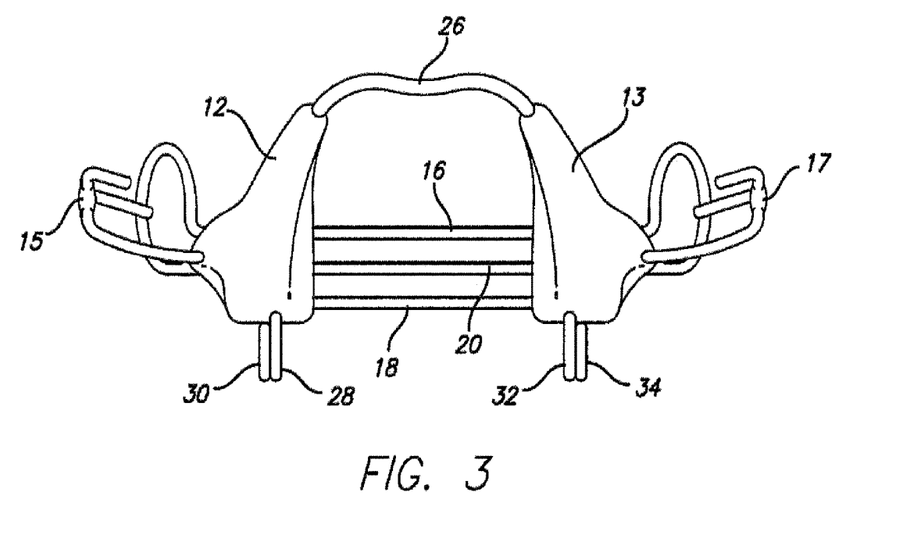
FIG. 3 is a rear elevational view of the appliance.
Figure 4:
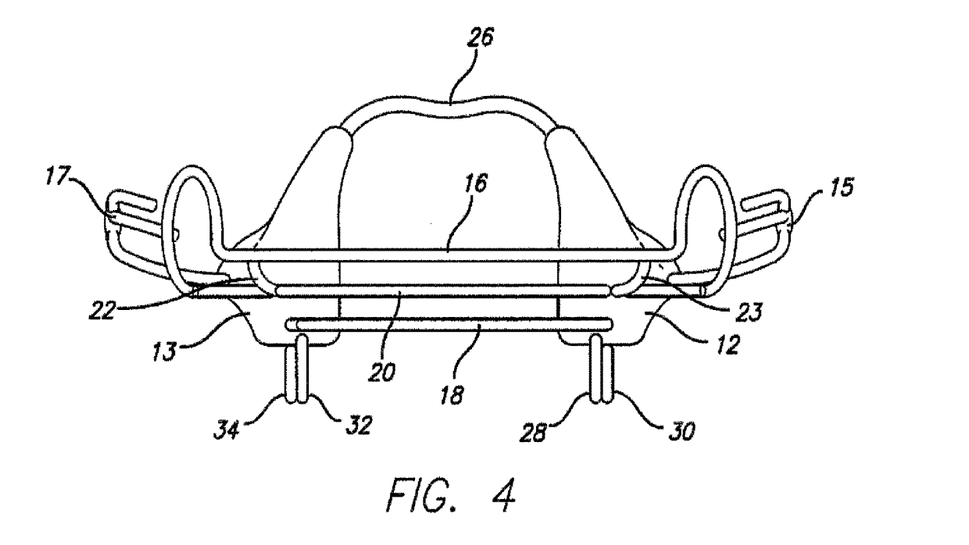
FIG. 4 is a front elevational view of the appliance.

Referring now to the drawings, there is shown the orthodontic appliance 10 of the invention embedded into two acrylic bases, right base 12 and left base 13. The appliance is attached to the upper teeth, by Hang Clasp 15 to upper left first permanent molar 14 and the upper left first permanent molar (not shown) by Hang Clasp 17 (see FIG. 2). The Hang Clasp, which is named by the inventor herein, is described in detail in U.S. Pat. No. 8,435,031, the disclosure of which is hereby incorporated in its entirety by reference herein.

A labial bow 16, located in the front region of the appliance, helps to keep the appliance seated against the upper teeth, mainly the upper incisors. The labial bow 16, combined with the two Hang Clasps on the primary molars, are adjusted so that the appliance will not move at all, unless a very substantial force is exerted to remove it from the mouth.

The lower incisor support wire 18 (along with one coming from the other side, not shown) is to help the patient know where to bite into the appliance. The lingual surface of the lower incisors contacts lower incisor support wire 18 and the patient knows that this is the correct position to bite into the appliance. Lower incisor support wires 18 are adjusted during the treatment to make sequential advancements of the lower jaw. For instance, if there is a 15 mm. space between the upper and lower front teeth (overjet) the lower jaw is advanced about 6-7 mm. during the initial advancement. The patient gets used to wearing the appliance in this position for a few days or weeks. Then, lower incisor support wires 18 are adjusted to get more advancement of the lower jaw. These increments are generally not more than 5 mm. per advancement. These wires 18 are adjusted sequentially until the space between the upper and lower incisors (overjet) is completely eliminated.

Upper incisor support wire 20 (along with one coming from the other side, not shown) function to prevent the upper front teeth from falling back. In every case, the upper incisors are advanced dramatically. This advancement is often 8-10 mm. forward in order to idealize the position of the upper front teeth in the face. Without some support, the upper front teeth will fall about a millimeter per day. Upper incisor support wires 20 provide support for the incisors and prevent them from falling back. They are small and do not impinge on the tongue space like a thick layer of acrylic would do. The object is to get the patient to posture the tip of their tongue to the palate just behind the upper front teeth. These wires 20 support the incisors without interfering with proper placement of the tongue at rest.

Lateral incisor support wires 22 and 23 function to prevent the lateral incisor from drifting distally (back) along the arch. All the upper incisor teeth have been advanced as part of the preparation of the upper teeth with the Hang Expancer. Otherwise, the lateral incisor teeth would want to drift back along the arch. Lateral incisor support wires 22 and 23 engage the distal aspect of the lateral incisors to prevent this from occurring.

Cuspid support wires 24 and 25 prevent the cuspids from moving medially (toward the midline) or distally (back along the line of the arch). The primary cuspids are advanced along with the incisor teeth as part of the preparation of the maxilla with the Hang Expancer. These teeth would tend to collapse medially and move distally without some means of support. The cuspid support wires engage the cuspids on the palatal gingival margin and distal gingival margin to prevent such movement from occurring.

Palatal bar 26 provides strength to connect the right and left side acrylic bases 12 and 13 of the Anterior Development and Postural Trainer (ADAPT-LGR) 10 appliance. Palatal bar 26 is very strong and provides a rigid connection of the right and left side acrylic bases 12, 13 without being bulky like a full palate of acrylic. Palatal bar 26 impinges on the tongue space only minimally and much less than a full palate of acrylic.

Figure 1:
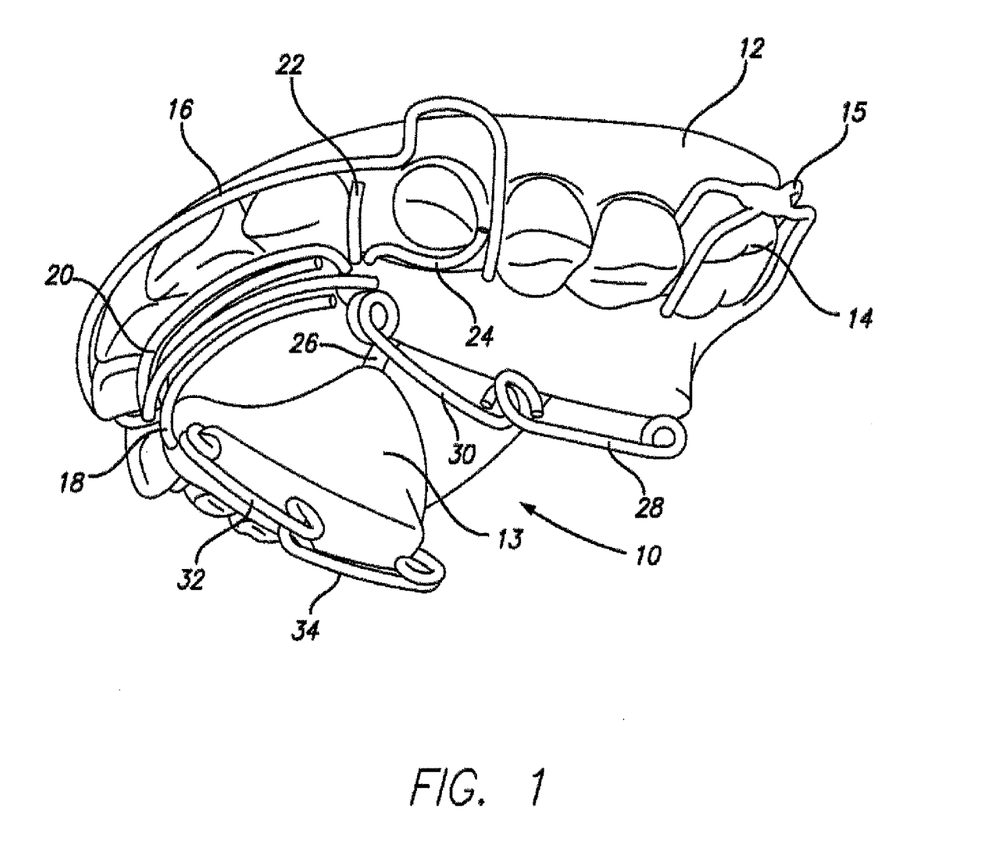
FIG. 1 is a perspective view of the orthodontic appliance of this invention.
Figure 5:
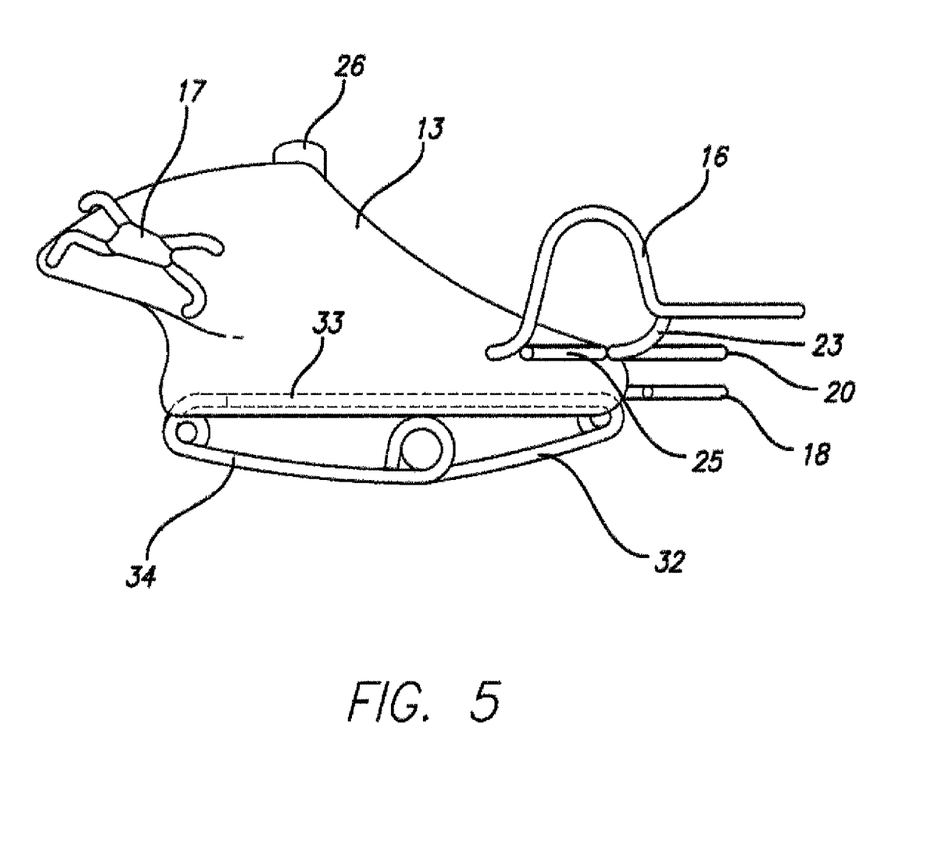
FIG. 5 is a right side view of the appliance, the left side being the same.
Figure 6:
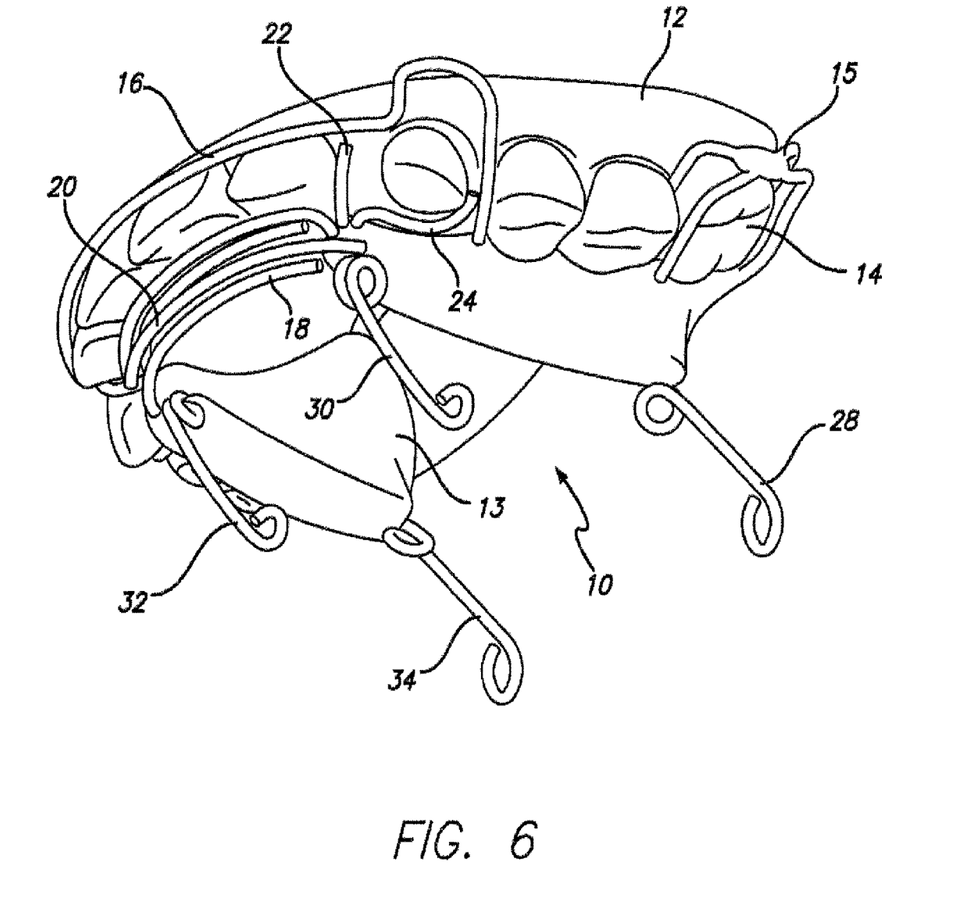
FIG. 6 is a perspective view with the landing gears open.
Figure 7:
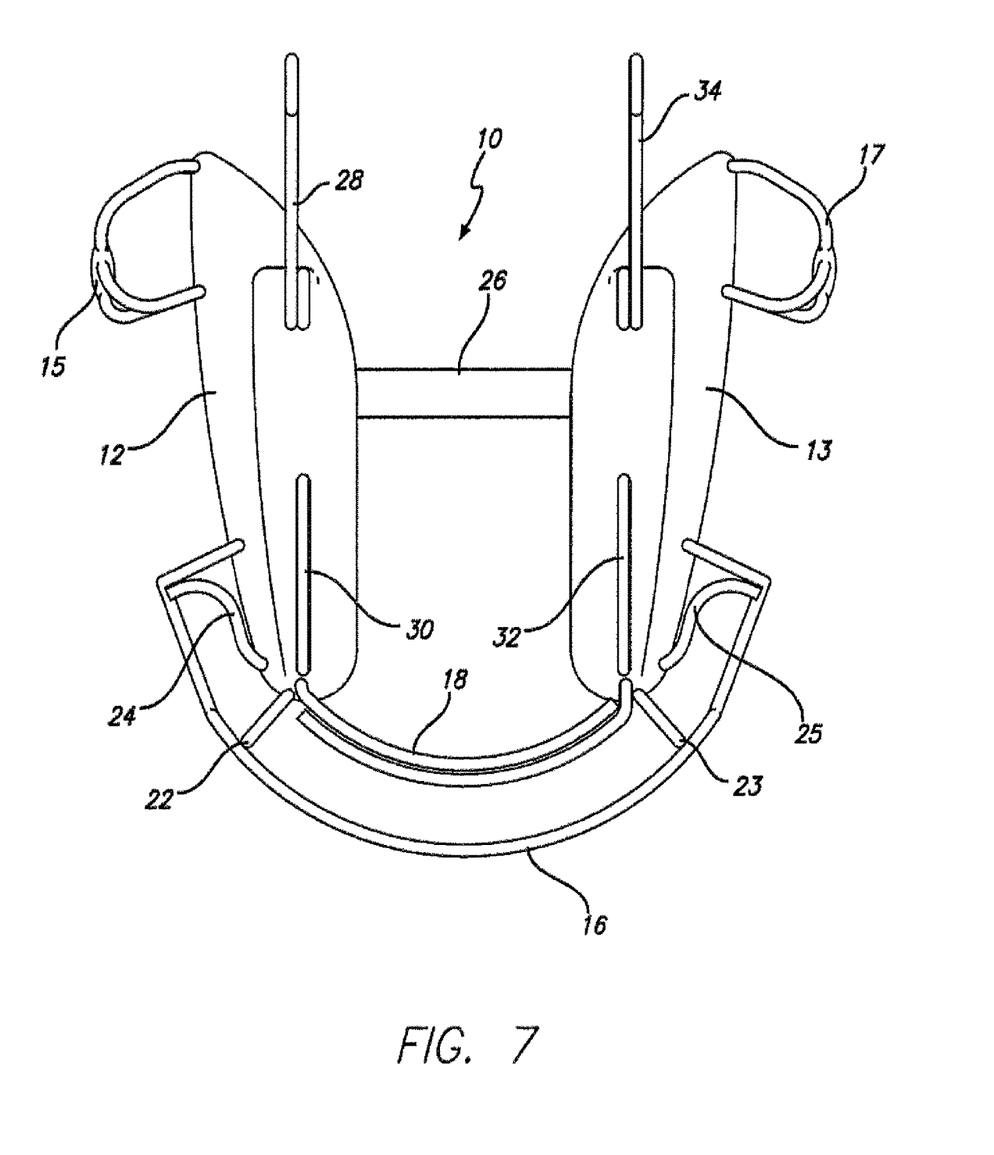
FIG. 7 is a bottom view with the landing gears open.
Figure 8:
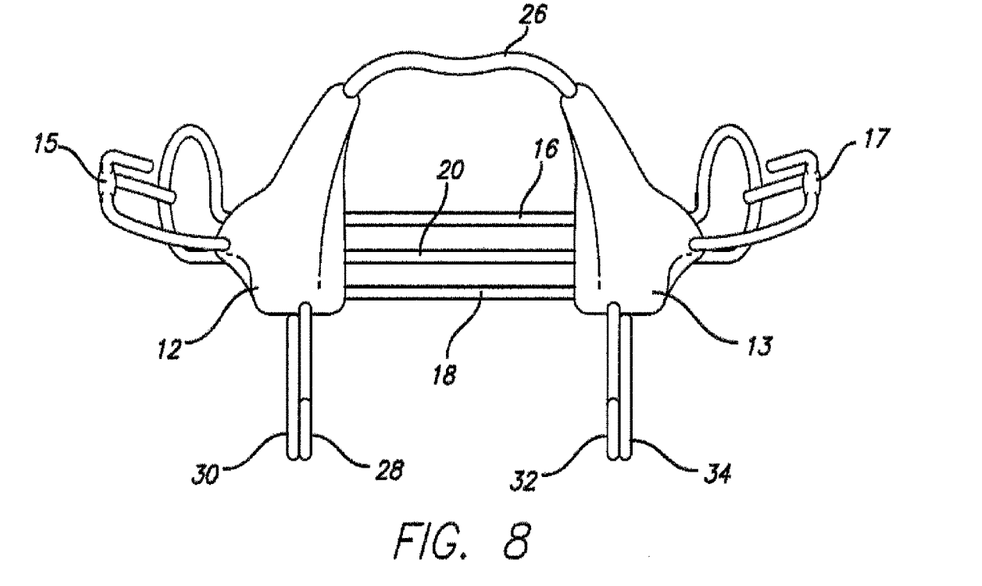
FIG. 8 is a rear elevational view of the appliance with the landing gears open.
Figure 9:
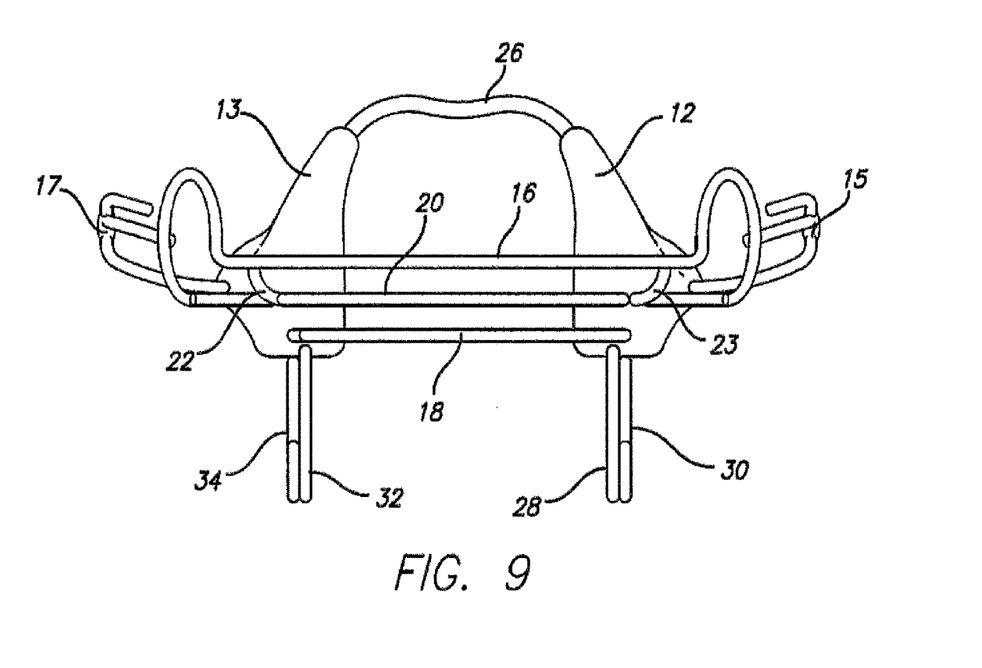
FIG. 9 is a front elevational view of the appliance with the landing gears open; and, FIG. 10 is a right side view with the landing gears open, the left side being the same.
Figure 10:
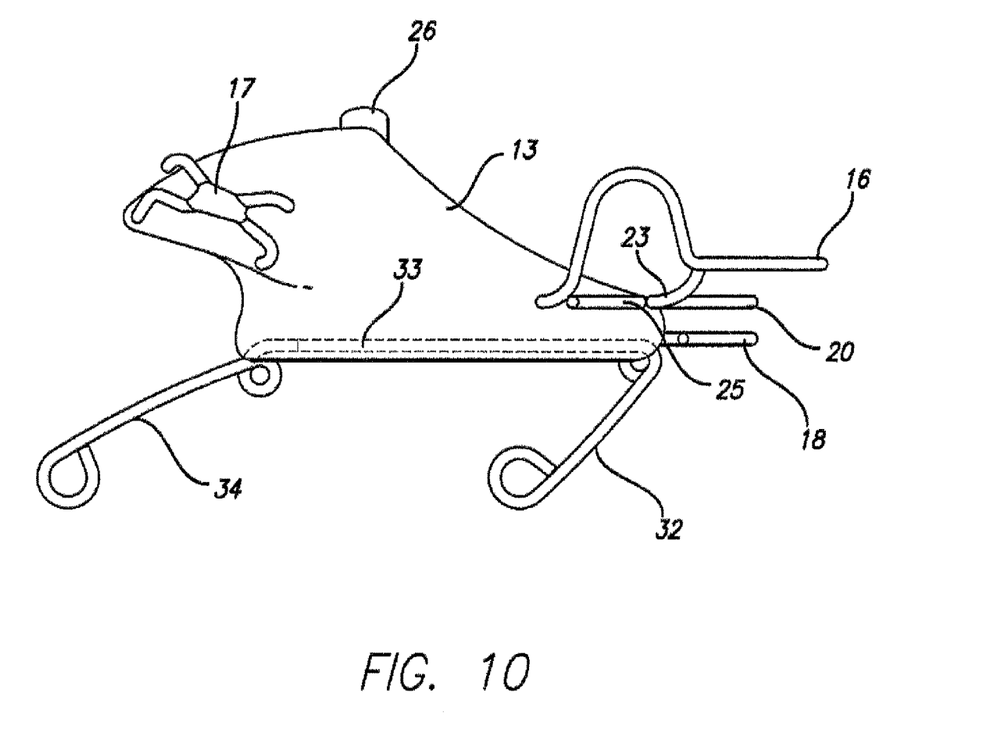

A plurality of landing gear reminders, preferably four landing gear reminders 28, 30, 32 and 34, function the same. They are first bent down to an approximate ideal position, as determined in the protocol of the treatment, basically as shown in FIGS. 1, 5 and 6. FIG. 5 shows how the landing gear reminders are held by wire portion 33 of each landing gear reminder held by acrylic 13. Small amounts of a hydroplastic material are then added to the landing gear reminders they are adjusted to engage the soft tissue covering the mandible near the floor of the mouth. Anterior landing gear reminders 30 and 32 are adjusted to function in the floor of the mouth in the region of the lower primary first molar. Posterior landing gears 28 and 34 function in the retromolar region of the mandible. The hydroplastic material is added in a soft state (softened with very warm water). The mandible is brought forward by the doctor into a protruded position and then "backed into position" against the hydroplastic material. The mandible is held in place for a few seconds while the material cools and hardens.

The patient then postures their jaw forward to get away from the landing gear reminder and open their mouth. The appliance is removed from the mouth and the hydroplastic material is cooled completely in cold water. The appliance is then placed back in the mouth to check the adjustment. Properly adjusted the patient must posture their jaw a bit too far forward initially and then "back" their jaw into position in the appliance. If their jaw wants to fall back and open in this position, the hydroplastic material touches the soft tissue and signals the patient not to allow the mandible to fall back. This can eliminate or dramatically reduce the "headgear effect" which will retract the upper arch. Alternatively, cold cure acrylic or another plastic material can be used for this adjustment rather than the hydroplastic material. Treatment success hinges on the doctor's ability to adjust the landing gear reminders properly, so the lower jaw does not fall back.

Posterior landing gears 28 and 34 act exactly the same as anterior landing gear reminders 30 and 32 except they function in the retromolar region of the mandible, to engage that area to keep the mandible from falling back.

Anterior landing gear reminder 32 and posterior landing gear reminder 34 function the same as described above for landing gear reminders 28 and 30.

As stated above, the landing gear reminders can easily be bent forward and adjusted to the proper length with one twist of the pliers. The thermoplastic material can be adjusted again to fully engage the landing gear reminders so that they are placed in the proper position. The posterior reminders overlap the anterior reminders when they are folded in the "up" position.

The ADAPT-LGR, landing gear reminders, are bent down to the proper position and then thermoplastic material is added which engages the soft tissue of the floor of the mouth. The patient's jaw is adjusted to the soft thermoplastic material when it is warm. It adapts intimately to the soft tissue of the floor of the mouth adjacent to the lower bicuspid teeth (anterior landing gear) and in the retromolar area (posterior landing gear.) Properly, it is adjusted so that the patient must keep their jaw forward and cannot allow it to exert a pull back on the appliance and hence on the upper teeth and jaw.

The number of landing gear reminders used depends upon the needs of the patient and can be from about 2 to about 6 or 8, with four landing gear reminders usually being best. The size of the landing gear reminders also depends upon the size and needs of the patient and the size of the entire appliance.

The wire utilized in this appliance is preferably stainless steel wire that may vary from about 0.036 mm to about 0.040 mm diameter. The 0.040 wire is best used for the landing gear reminders, as it is a bit stiffer and does not move easily. It is less subject to being bent by a child who is not as careful as they should be when the appliance is out of the mouth.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An orthodontic appliance adapted to be attached to the upper teeth using clasps, comprising;
   a. two upper acrylic palate bases;
   b. a labial bow located in a front region of the appliance;
   c. two lower incisor support wires located in a front region of the appliance;
   d. two upper incisor support wires located in a front region of the appliance;
   e. two lateral incisor support wires located in the front region of the appliance;
   f. two cuspid support wires located in a front region of the appliance;
   g. a palatal bar which connects the two acrylic bases together; and,
   h. a plurality of wire landing gear reminders, a wire portion of a landing gear reminder attached to an acrylic base and another wire portion of a landing gear reminder adapted to posture a patient's lower jaw forward; and,
   i. further comprising hydroplastic material added to the end of the landing gear reminders that are adapted to engage with the soft tissue covering the mandible.

2. The appliance of claim 1 in which the landing gear reminders can easily be bent forward and adjusted to a proper length.

3. The appliance of claim 1 in which the labial bow is capable of keeping the appliance seated against the upper teeth.

4. The appliance of claim 1 in which the lower incisor wires are capable of contacting the lingual surface of the lower incisors and the lower incisor wires are also capable of making sequential advancements of the lower jaw.

5. The appliance of claim 4 in which the lower incisor support wires are capable of contacting the lingual surface of the lower incisors so that a patient knows that this is the correct position to bite into the appliance.

6. The appliance of claim 1 in which the upper incisor support wires are capable of preventing the upper front teeth from falling back.

7. The appliance of claim 1 in which the cuspid support wires are capable of preventing the cuspids from moving medially and distally.

8. The appliance of claim 1 in which four landing gear reminders are utilized.

9. The appliance of claim 1 in which the landing gear reminders are folded up until they are needed.

10. The appliance of claim 1 in which the hydroplastic material is added in a soft state and the mandible is held in place for a few seconds for the material to cool and harden.

11. The appliance of claim 10 in which the appliance is removed from the mandible and the hydroplastic material is cooled completely in cold water and the appliance is then placed back in the mandible to check the adjustment.

12. The appliance of claim 1 further comprising anterior landing gear reminders which function in the floor of the mouth and posterior landing gear reminders which function in the retromolar region of the mandible to keep the mandible from falling back.

13. The appliance of claim 1 in which the landing gear reminders are made of stainless steel wire.

14. The appliance of claim 1 in which the landing gear reminders are first bent down to an approximate ideal position as determined in a protocol of the treatment.

15. The appliance of claim 14 in which the landing gear reminders can easily be bent forward and adjusted to a proper length with a common tool.

16. An orthodontic appliance that is capable of posturing the lower jaw forward and is adapted to connect the lower jaw to the upper jaw, the appliance adapted to attached to the upper teeth using clasps, comprising:
 a. two acrylic upper palate bases;
 b. a labial bow located in a front region of the appliance capable of keeping the appliance seated against the upper incisors;
 c. two lower incisor support wires located in a front region of the appliance, the two lower incisor wires capable of contacting the lingual surface of the lower incisors;
 d. two upper incisor support wires located in a front region of the appliance adapted to prevent the upper teeth from falling back;
 e. two lateral incisor support wires located in the front region of the appliance adapted to prevent the lateral incisors from drifting back;
 f. two cuspid support wires located in a front region of the appliance adapted to prevent the cuspids from moving medially or distally back;
 g. a strong palatal bar which connects the two acrylic bases together; and,
 h. four wire landing gear reminders; and,
 i. a wire portion of each landing gear reminder attached to an acrylic base and another wire portion of each landing gear reminder adapted to posture a patient's lower jaw forward; and,
 j. further comprising a hydroplastic material added to the landing gear reminders which are adapted to engage the soft tissue covering the mandible.

17. The appliance of claim 16 in which the hydroplastic material is added in a soft state and the mandible is held in place for a few seconds for the material to cool and harden.

18. The appliance of claim 17 in which the appliance is removed from the mandible and the hydroplastic material is cooled completely in cold water and the appliance is then placed back in the mandible to check the adjustment.

* * * * *